(12) United States Patent
Masini

(10) Patent No.: US 7,044,132 B2
(45) Date of Patent: May 16, 2006

(54) SURGICAL DRAPE ADAPTED FOR USE WITH RADIOLOGICAL EQUIPMENT

(75) Inventor: Michael A. Masini, Ann Arbor, MI (US)

(73) Assignee: MedIdea, LLC, Ann Arbor, MI (US)

( * ) Notice: Subject to any disclaimer, the term of this patent is extended or adjusted under 35 U.S.C. 154(b) by 267 days.

(21) Appl. No.: 10/214,535

(22) Filed: Aug. 8, 2002

(65) Prior Publication Data

US 2004/0025886 A1 Feb. 12, 2004

(51) Int. Cl.
*A61B 19/00* (2006.01)
*A61B 19/08* (2006.01)

(52) U.S. Cl. ............... 128/849; 128/850; 128/851; 128/852; 128/853; 128/854; 128/855; 128/856

(58) Field of Classification Search ........... 128/849, 128/851, 852, 853, 854, 855, 856
See application file for complete search history.

(56) References Cited

U.S. PATENT DOCUMENTS

| | | | | | |
|---|---|---|---|---|---|
| 4,476,860 | A | * | 10/1984 | Collins et al. | 128/853 |
| 4,664,103 | A | * | 5/1987 | Martin et al. | 128/852 |
| 4,869,271 | A | * | 9/1989 | Idris | 128/853 |
| 4,873,997 | A | * | 10/1989 | Marshall | 128/849 |
| 4,889,135 | A | * | 12/1989 | Poettgen | 128/849 |
| 4,889,136 | A | * | 12/1989 | Hanssen | 128/855 |
| 4,905,710 | A | * | 3/1990 | Jones | 128/849 |
| 4,945,924 | A | * | 8/1990 | Poettgen | 128/849 |
| 4,957,120 | A | * | 9/1990 | Grier-Idris | 128/849 |
| 4,976,274 | A | * | 12/1990 | Hanssen | 128/849 |
| 5,042,507 | A | * | 8/1991 | Dowdy | 128/849 |
| D333,404 | S | * | 2/1993 | Thompson | D6/602 |
| 5,209,243 | A | * | 5/1993 | Glassman | 128/849 |
| 5,222,507 | A | * | 6/1993 | Taylor | 128/849 |
| 5,299,582 | A | * | 4/1994 | Potts | 128/846 |
| 5,341,821 | A | * | 8/1994 | DeHart | 128/849 |
| 5,383,476 | A | * | 1/1995 | Peimer et al. | 128/849 |
| 5,388,593 | A | * | 2/1995 | Thomalla | 128/849 |
| 5,394,891 | A | * | 3/1995 | Mills et al. | 128/852 |
| 5,398,700 | A | * | 3/1995 | Mills et al. | 128/853 |
| 5,409,018 | A | * | 4/1995 | Mills | 128/852 |
| 5,413,118 | A | * | 5/1995 | Thompson | 128/853 |
| 5,454,381 | A | * | 10/1995 | DeHart | 128/849 |
| 5,464,024 | A | * | 11/1995 | Mills et al. | 128/849 |

(Continued)

*Primary Examiner*—Henry Bennett
*Assistant Examiner*—Nihir Patel
(74) *Attorney, Agent, or Firm*—Gifford, Krass, Groh, Sprinkle, Anderson & Citkowski, PC

(57) ABSTRACT

A surgical drape provides a volume to accommodate radiological equipment such as a C-arm x-ray device without pulling the bottom of the drape up which could otherwise interrupt the sterile field. In one preferred embodiment, the space is created with pleated or gathered section, which receives the equipment as it is brought up laterally without lifting any portion of the material overall. A different embodiment of the invention includes a tunnel or tent formed in the material, generally without pleating. In this case, the tunnel or tent extends from the bottom of the drape to or above a patient-contacting procedural area. As a further option, in either the pleated or shaped configurations, additional material may be included to form a slit to further shroud the radiological equipment when positioned for a medial-lateral exposure. As yet a further option to all embodiments, the bottom edge of the drape may include an adhesive, integral weights, or both, to keep the bottom edge in close proximity, or actually adhered, to the floor, to further prevent lifting.

8 Claims, 4 Drawing Sheets

U.S. PATENT DOCUMENTS

| | | | |
|---|---|---|---|
| 5,464,025 A * | 11/1995 | Charles et al. | 128/849 |
| 5,471,999 A * | 12/1995 | Mills | 128/849 |
| 5,513,655 A * | 5/1996 | Peimer et al. | 128/849 |
| D370,822 S * | 6/1996 | Palomo et al. | D6/602 |
| 5,586,563 A * | 12/1996 | Newman | 128/849 |
| 5,592,952 A * | 1/1997 | Bohn | 128/849 |
| 5,611,356 A * | 3/1997 | Rothrum | 128/844 |
| 5,640,975 A * | 6/1997 | Diao | 128/853 |
| 5,647,376 A * | 7/1997 | Thompson | 128/853 |
| 5,765,566 A * | 6/1998 | Rothrum | 128/849 |
| 5,778,890 A * | 7/1998 | Lofgren et al. | 128/849 |
| 5,778,891 A * | 7/1998 | McMahan | 128/849 |
| 5,803,086 A * | 9/1998 | Scholz et al. | 128/849 |
| 5,860,420 A * | 1/1999 | Wiedner et al. | 128/853 |
| 6,055,987 A * | 5/2000 | Griesbach et al. | 128/849 |
| 6,138,676 A * | 10/2000 | Bruhn | 128/849 |
| 6,199,553 B1 | 3/2001 | Hafer et al. | 128/849 |
| 6,923,186 B1* | 8/2005 | Gavette et al. | 128/854 |
| 2003/0060831 A1* | 3/2003 | Bonutti | 606/86 |

* cited by examiner

SURGICAL DRAPE ADAPTED FOR USE WITH RADIOLOGICAL EQUIPMENT

FIELD OF THE INVENTION

This invention relates generally to surgical drapes of the type used to maintain a sterile field and, in particular, to a drape better suited for use with certain types of radiological equipment, particularly C-arm configurations found in trauma and other environments.

BACKGROUND OF THE INVENTION

The introduction of certain types of radiological equipment, such as C-arm x-ray machines have markedly improved the ability of surgeons and other health care professionals to obtain a rapid assessment of a patient's condition, including fractures and other trauma-related conditions in emergency-room settings. In such situations, it is general practice to position the patient in a frame used for traction or other stabilization. A surgical drape is used to separate the patient from the attending physician.

Existing drapes of this kind, shown in FIG. 1, generally consist of a relatively large piece of transparent material 102, including an area 122 having an adhesive which is applied to the skin of a patient 120 in the area wherein a procedure will be carried out. The adhesive area is generally of a different color, such as yellow, and includes a release layer to expose the sticky surface. The top of the drape 102 is generally attached overhead, as to some component of the framework 104, which may or may not include a central bar 106, with the remainder of the material hanging down in the vicinity or onto the floor.

Such a configuration would be entirely acceptable, where it not for the need to bring in the radiological equipment before, during, or after the procedure. In positioning a C-arm 110, for example, one portion of the arm must often be brought forward and up relative to the lateral side of the patient. When this occurs, a portion of the equipment comes in contact with the surgical drape and, in fact, causes a portion of the drape below the procedure area to be brought up to, or above, waist level, as indicated by the upwardly pointing arrow.

This is undesirable, since it is well known that any material previously below the procedural area is considered to be out of the sterile field. If the drape is brought up to waist level or higher, the sterile field is compromised. Although some surgeons attempt to pull down on the raised lower end of the drape to keep it below the level of sterility, it is very difficult to properly maintain the sterile field, since there is no extra material of the drape to accommodate the pivoting C-arm.

SUMMARY OF THE INVENTION

This invention improves upon the existing art by providing a surgical drape with additional material on either or both sides of the procedural area to accommodate radiological equipment such as a C-arm x-ray device without pulling the bottom of the drape up and interrupting the sterile field.

In one preferred embodiment, the extra material takes the form of a pleated or gathered section, which receives the equipment as it is brought up laterally without lifting any portion of the material overall. A further embodiment of the invention includes a tunnel or tent formed in the material, generally without pleating. In this case, the tunnel or tent extends from the bottom of the drape at least to a point above the procedural area, again, to receive the equipment as it is brought up for use. A different embodiment features a flap that may, or may not, be rolled up or otherwise retained against the vertically hanging drape, and extended outwardly, permitting attachment to an instrument table, Mayo stand, or the like.

As a further option, in each of the various configurations, a slit may be formed in the vertically hanging material to further shroud the radiological equipment, particularly when positioned for a medial-lateral exposure. Also in each embodiment, the drape may include an adhesive, integral weights, or both, to keep the bottom edge in close proximity, or temporarily adhered to the floor to further prevent lifting.

DETAILED DESCRIPTION OF THE INVENTION

Figure 1:
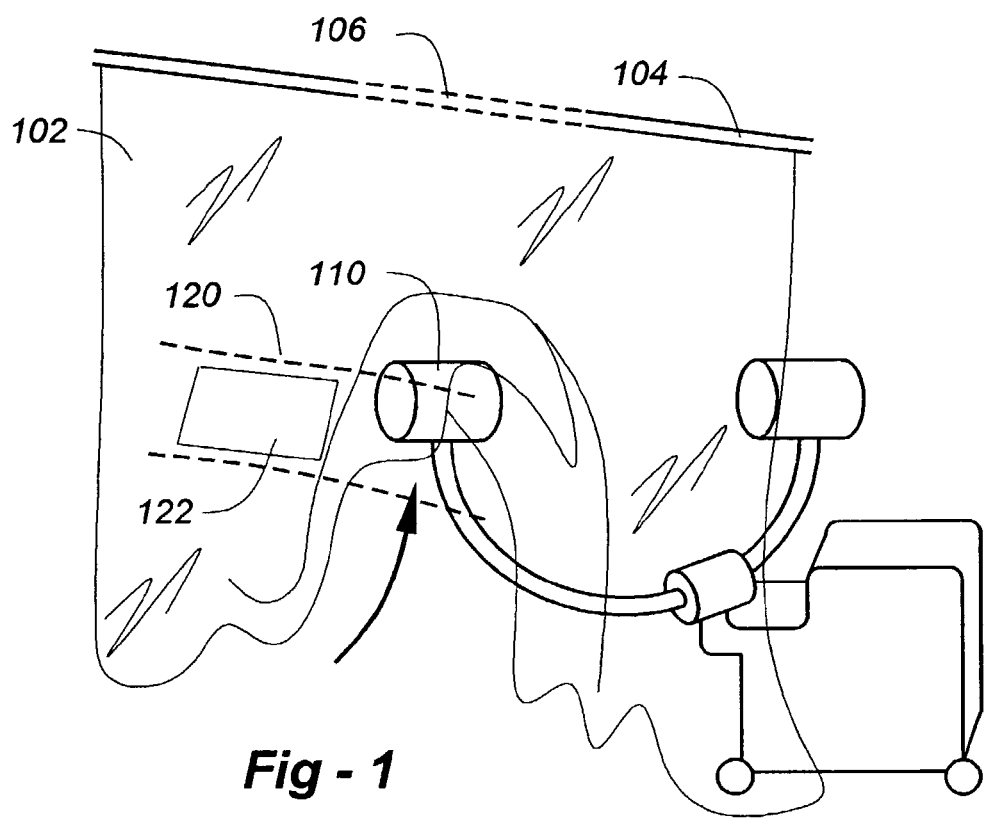
FIG. 1 is a drawing of a prior-art surgical drape in use, illustrating problems addressed by the instant invention.
Figure 2:
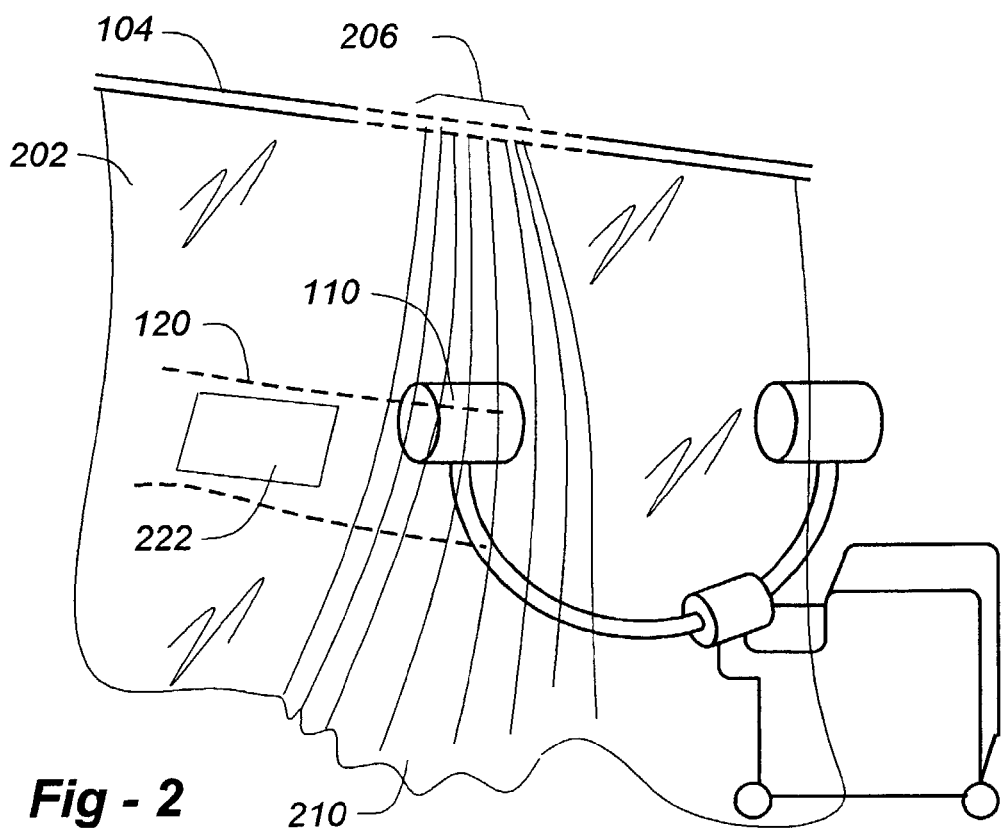
FIG. 2 is a drawing of a preferred embodiment of the invention, including a pleated or gathered section to accommodate a piece of radiological equipment such as a C-arm x-ray head.

Having discussed the problems of the prior art, FIG. 2 shows a surgical drape according to the invention generally at 202, including a pleated or gathered section 206, 210, which allows the C-arm to come up and down without substantially raising the bottom section of the drape 210. As with existing drapes, an area 222 may be provided with an adhesive applied to the skin of a patient 120 in the area wherein a procedure will be carried out.

Figure 3:
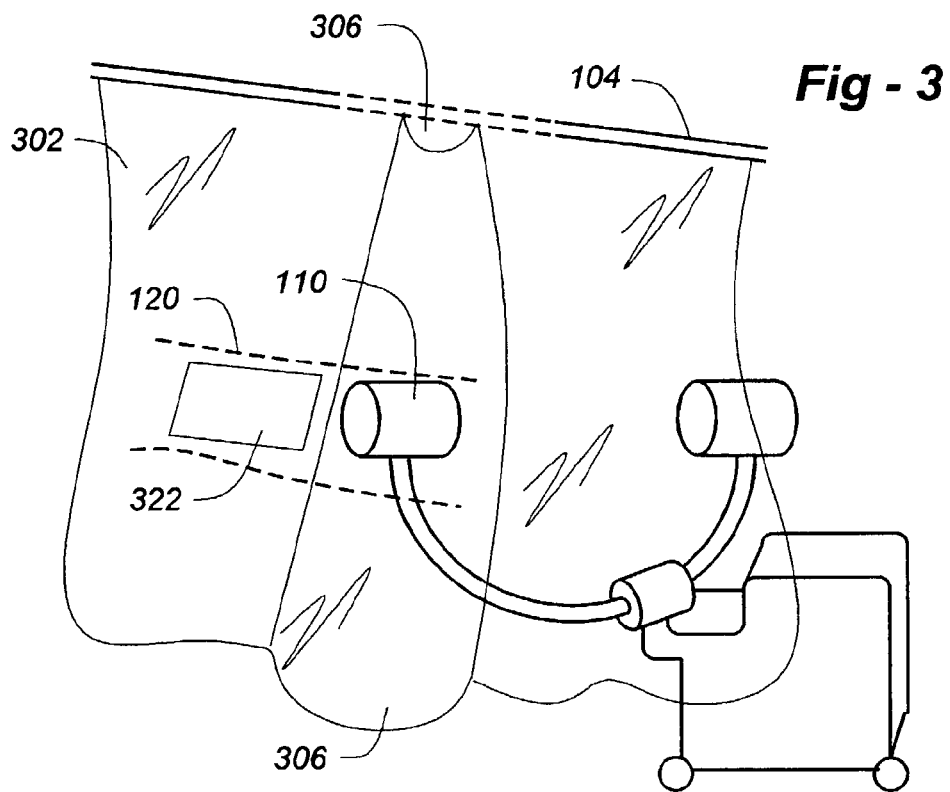
FIG. 3 is a drawing of an alternative embodiment, involving a formed tunnel, and in this case without pleating or gathering.
Figure 4:
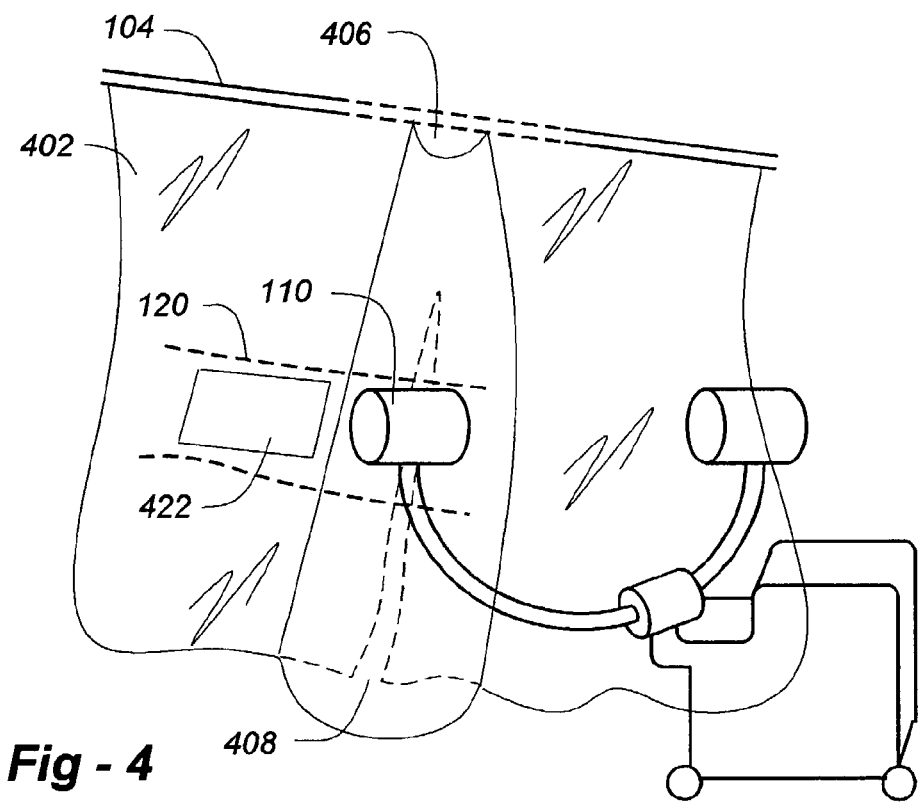
FIG. 4 is a cross-section drawing showing the way in which optional material may be added to form a slit to receive a radiological equipment.

FIG. 3 illustrates an embodiment of the invention including a formed tunnel 406. FIG. 4 shows how extra material may be added to provide a slit 408. Adhesive areas 322, 422 may optionally be provided.

Figure 5:
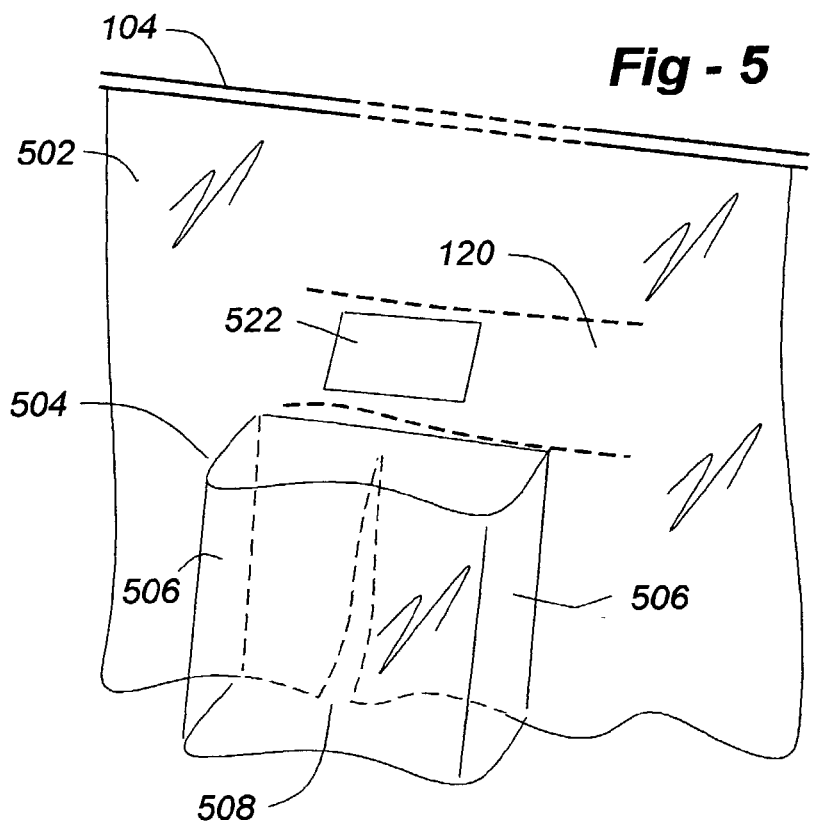
FIG. 5 is a drawing which shows a tent structure more appropriate to trauma situations.
Figure 6:
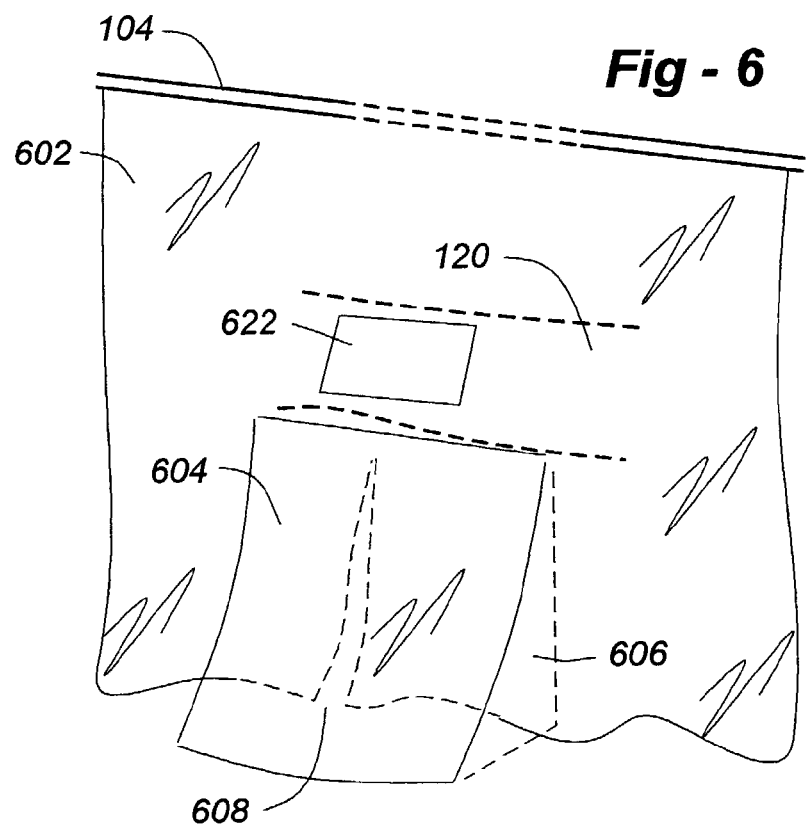
FIG. 6 is a drawing which shows an alternative embodiment including a hinged flap structure.

While the configurations so far describe work well in hip fractures, in trauma situations the embodiments of FIGS. 5 and 6 may be more appropriate. In FIG. 5, material is added to form what amounts to a tent structure. Slit 508 may optionally be provided at the back wall of the tent. Should the C-arm raise the tent somewhat during use side panels 506 are preferably provided. The structure of FIG. 6 more resembles a hinged flap. Side panels 606 and 608 are optional. Adhesive areas 322, 422 may optionally be provided.

Figure 7:
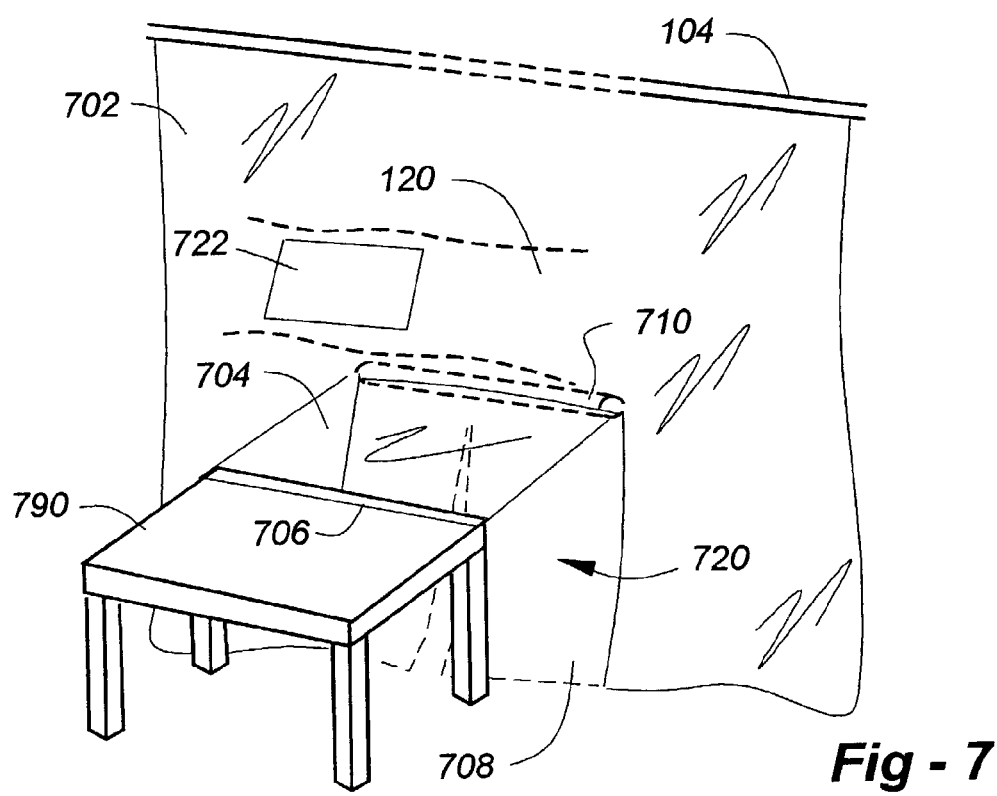
FIG. 7 is a drawing which shows how an outwardly extending flap according to the invention may be temporarily adhered to a Mayo stand or other type of table or instrumentation.

FIG. 7 is a drawing which shows how an outwardly extending flap 704 according to the invention may be temporarily adhered to a Mayo stand 790 or other type of table or instrumentation. The edge 706 of the flap 704 may be attached with tape, clips, weights, and so forth, and may be rolled up against (710) or otherwise held against the sheet 702 when not extended. Slitted area 708 and side panels at 720 may optionally be provided. The patient-contacting adhesive is shown at 722.

Figure 8:
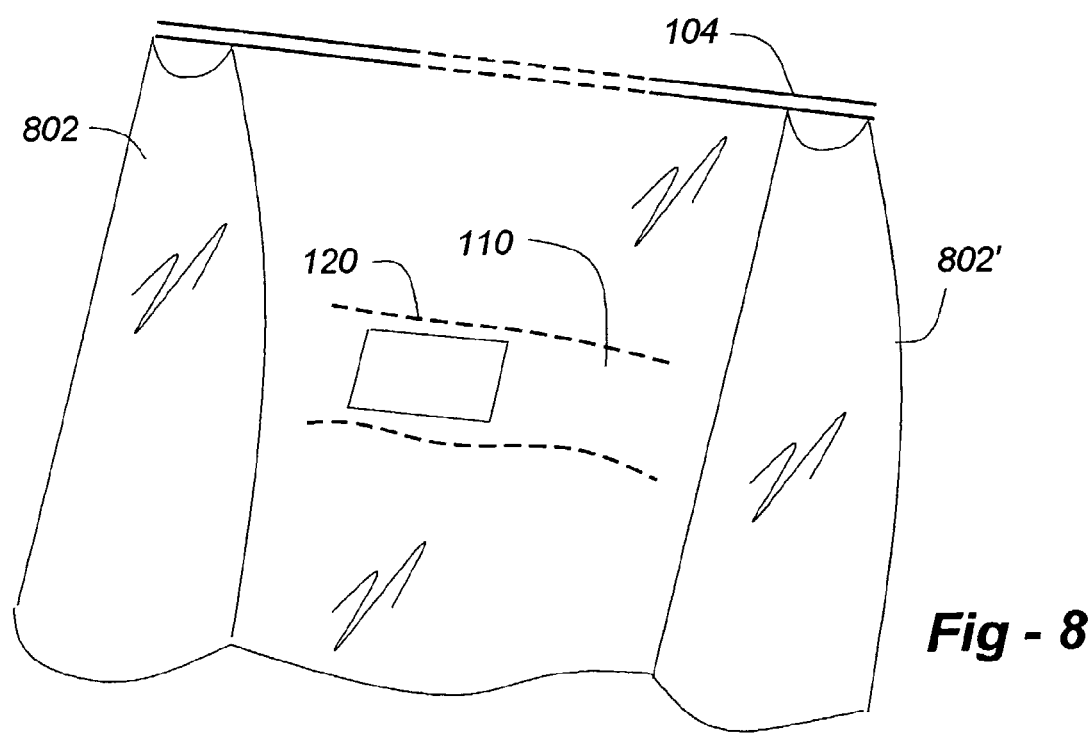
FIG. 8 is a drawing which shows how a drape according to the invention may incorporate multiple channels or spaces for receiving radiological equipment.

It will be appreciated that the invention is not limited to a single channel for receiving radiological or other euipment. FIG. 8 is a drawing which shows how a drape according to the invention may incorporate multiple channels or spaces (802, 802') for receiving such equipment. Such a configuration is particularly useful in performing right- and left-side procedures.

Although not shown, in all of the various embodiments elastic material may be added to enhance expansion, particularly where the gatherings, tunnel, tent or flap structures attach or transition to the drape itself. Weights or adhesive may also be added, particularly along the bottom section to further ensure that the curtain does not ride up as the C-arm is raised. As yet a further option, a topical antibiotic may be included in the patient-contacting adhesive area.

I claim:

1. A surgical drape adapted for use with equipment such as a C-arm requiring occasional positioning above a sterile field, the drape comprising:
    a sheet of flexible material configured to hang in a vertical plane with a top edge, a bottom edge, a patient-facing side and a physician-facing side;
    an area of adhesive on the patient-facing side facilitating patient contact to perform a surgical procedure through that area of the drape;
    material extending outwardly from the vertical plane on the physician-facing side providing a space to receive the equipment as it is raised to minimize lifting of the bottom edge of the sheet; and
    wherein the sheet is open behind the material extending outwardly from the vertical plane on the physician-facing side.

2. The surgical drape of claim 1, wherein the material extending outwardly from the vertical plane on the physician-facing side is in the form of a vertically oriented tunnel.

3. The surgical drape of claim 1, wherein the sheet is at least semi-transparent.

4. The surgical drape of claim 1, wherein the area of adhesive further includes a topical antibiotic.

5. A surgical drape adapted for use with equipment such as a C-arm requiring occasional positioning above a sterile field, the drape comprising:
    a sheet of flexible material configured to hang in a vertical plane with a top edge, a bottom edge, a patient-facing side and a physician-facing side;
    an area of adhesive on the patient-facing side facilitating patient contact to perform a surgical procedure through that area of the drape;
    material extending outwardly from the vertical plane on the physician-facing side providing a space to receive the equipment as it is raised to minimize lifting of the bottom edge of the sheet; and
    wherein the sheet is slit from the bottom edge behind the material extending outwardly from the vertical plane on the physician-facing side.

6. The surgical drape of claim 1, wherein the material extending outwardly from the vertical plane on the physician-facing side is in the form of a vertically oriented tunnel.

7. The surgical drape of claim 1, wherein the sheet is at least semi-transparent.

8. The surgical drape of claim 1, wherein the area of adhesive further includes a topical antibiotic.

* * * * *